(12) United States Patent
Ross

(10) Patent No.: US 6,264,693 B1
(45) Date of Patent: Jul. 24, 2001

(54) AIR ABRASIVE TEXTURING PROCESS FOR INTRAOCULAR IMPLANTS

(75) Inventor: Mark Wesley Ross, Costa Mesa, CA (US)

(73) Assignee: Bausch & Lomb Surgical, Inc., Claremont, CA (US)

( * ) Notice: Subject to any disclaimer, the term of this patent is extended or adjusted under 35 U.S.C. 154(b) by 0 days.

(21) Appl. No.: 09/209,551

(22) Filed: Dec. 11, 1998

(51) Int. Cl.$^7$ .................................................. A61F 2/16
(52) U.S. Cl. ........................................ 623/6.17; 351/177
(58) Field of Search .................................. 623/6.17, 6.11, 623/4.1, 5.11; 351/177; 359/571

(56) References Cited

U.S. PATENT DOCUMENTS

| | | | |
|---|---|---|---|
| 4,605,409 | 8/1986 | Kelman | 623/6 |
| 4,676,791 | 6/1987 | LeMaster et al. | 623/6 |
| 4,769,956 | 9/1988 | Wern | 51/421 |
| 4,774,036 | 9/1988 | LeMaster et al. | 264/1.7 |
| 5,192,319 | 3/1993 | Worst | 623/6 |
| 5,549,670 | * 8/1996 | Young et al. | 623/6 |
| 5,578,080 | * 11/1996 | McDonald | 623/6 |
| 5,578,081 | * 11/1996 | McDonald | 623/6 |

FOREIGN PATENT DOCUMENTS

| | | |
|---|---|---|
| 26 41 120 | 3/1977 | (DE) . |
| 2571277 | 4/1986 | (FR) . |
| 1118545 | 4/1970 | (GB) . |
| WO 95/14552 | 6/1995 | (WO) . |

OTHER PUBLICATIONS

Lares Research Promotional Publication for The Director+ ™.

Lares Research Promotional Publication for The Associate + ™.

Lares Research Promotional Publication for The Producer™.

* cited by examiner

*Primary Examiner*—Dinh X. Nguyen
(74) *Attorney, Agent, or Firm*—Rita D. Vacca

(57) ABSTRACT

A process for imparting a glare resistant zone to an intraocular implant such as an intraocular lens using a highly regulated spray of an abrasive material. The spray is preferably of air and aluminum oxide, which may be washed from the intraocular implant during cleaning and polishing thereof. The process is suitable for any machinable intraocular lens material such as acrylates, methacrylates and hydrogels.

80 Claims, 2 Drawing Sheets

AIR ABRASIVE TEXTURING PROCESS FOR INTRAOCULAR IMPLANTS

FIELD OF THE INVENTION

The present invention relates to an air abrasive texturing process for use in the production of ophthalmic devices. More particularly, the present invention relates to an air abrasive texturing process and equipment necessary for the air abrasive texturing process to impart non-halo-inducing surfaces on intraocular lenses.

BACKGROUND OF THE INVENTION

For many years, the usual method of treating a diseased intraocular lens has been to remove the diseased lens and replace it with an IOL implant. Two surgical procedures have each been found useful in the removal of a diseased lens, i.e., extracapsular cataract extraction and phacoemulsification. Extracapsular cataract extraction involves the removal of a diseased lens in a relatively intact condition through the use of forceps or an instrument similar thereto. Phacoemulsification involves contacting a diseased lens of an eye with a vibrating cutting tip of an ultrasonically driven surgical handpiece to emulsify the lens. Once emulsified, the lens is aspirated from the eye. Both surgical procedures require the cornea (or sclera) and the anterior lens capsule of the eye to be opened to allow access to the interior of the lens capsule. Once within the lens capsule, the diseased lens is removed and an intraocular lens (IOL) implant is positioned therein.

Visual acuity deficiencies such as myopia (nearsightedness) and hyperopia (farsightedness) are typically corrected with the use of refractive lenses such as spectacles or contact lenses. Although these types of lenses are effective in correcting a wearer's eyesight, many wearers consider the lenses inconvenient. The lenses must be located, worn at certain times, removed periodically and may be lost or misplaced. The lenses may also be dangerous or cumbersome if the wearer participates in athletic activities or suffers an impact in an area near the eyes.

The use of surgically implanted IOLs as a permanent form of refractive correction has been gaining in popularity. As noted above, IOL implants have been used for years in aphakic eyes as replacements for diseased natural crystalline lenses, which have been surgically removed from the eyes. Many different IOL designs have been developed over past years and proven successful for use in aphakic eyes. The successful IOL designs to date primarily include an optic portion with supports therefor, called haptics, connected to and surrounding at least a part of the optic portion. The haptic portions of an IOL are designed to support the optic portion of the IOL in either the anterior or posterior of an eye.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. More rigid IOLs must be inserted through an incision in the cornea slightly larger than the diameter of the IOL's optic portion. Larger incisions have been found to be associated with an increased incidence of postoperative complications such as induced astigmatism.

After IOL implantation in either phakic or aphakic eyes, some patients experience visual distortions commonly referred to as "halos". Halo visual distortions are caused by light entering a patient's eye reflecting off of the edge of the IOL. For this reason, some IOLs are produced with glare reduction zones. Glare reduction zones are typically located around an outer peripheral edge of the optic portion of the IOL and may be colored, opaque or patterned to block or diffuse light.

Unfortunately, depending on the style and material of the IOL, manufacturing an IOL with a glare reduction zone using today's techniques is often times difficult and in some cases impossible for a variety of reasons.

Because of the noted shortcomings in today's techniques for imparting a glare reduction zone on IOL implants, there is a need for a process capable of imparting a glare reduction zone on most if not all IOL styles to minimize halo visual distortions and the like.

SUMMARY OF THE INVENTION

An intraocular lens (IOL) made in accordance with the present invention has an optic portion with an outer peripheral edge and at least one but preferably two or more haptic elements for supporting the optic portion in a patient's eye. The subject IOL is preferably formed of any suitable foldable or compressible IOL material known to those skilled in the art. Each haptic element preferably has an inner portion and an outer portion with the inner portion being connected to the outer peripheral edge of the optic portion. Each haptic element also preferably includes at least one contact plate on the outer portion and a central portion that extends between the contact plate and the inner portion. The contact plates are designed to engage an inner surface of a patient's eye.

Each IOL manufactured in accordance with the present invention has a glare reduction zone adjacent to an outer peripheral edge of the IOL's optic portion for reducing glare when struck by light entering the eye during high light or at times when the eye's pupil is dilated. The glare reduction zone is produced on the IOL using a highly regulated low-pressure spray of powder to impart an abraded pattern on the surface of the IOL in the desired location and pattern.

Accordingly, it is an object of the present invention to provide intraocular lenses with a glare reduction zone for use in phakic or aphakic eyes.

Another object of the present invention is to provide a process for producing a glare reduction zone on a variety of intraocular lens styles.

Another object of the present invention is to provide intraocular lenses for use in phakic or aphakic eyes, which minimize halo visual distortions.

Another object of the present invention is to provide a process for producing a glare reduction zone on a variety of intraocular lens materials.

Still another object of the present invention is to provide equipment suitable for a process for producing a glare reduction zone on a variety of intraocular lens styles and materials.

These and other objectives and advantages of the present invention, some of which are specifically described and others that are not, will become apparent from the detailed description, drawings and claims that follow wherein like features are designated by like numerals.

DETAILED DESCRIPTION OF THE INVENTION

Figure 1:
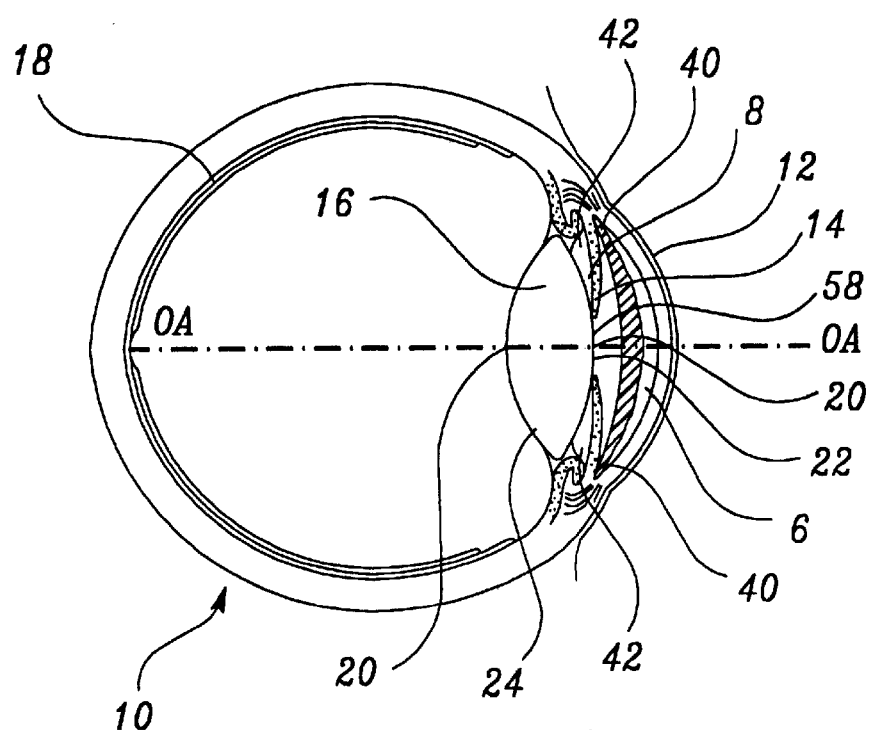
FIG. 1 is a schematic representation of the interior of a human eye including a natural lens and a refractive IOL implanted in the anterior chamber of the eye.

FIG. 1 illustrates a simplified diagram of an eye 10 showing landmark structures relevant to the implantation of an intraocular lens of the present invention. Eye 10 includes an optically dear cornea 12 and an iris 14. A natural crystalline lens 16 and a retina 18 are located behind the iris 14 of eye 10. Eye 10 also includes anterior chamber 6 located in front of iris 14 and a posterior chamber 8 located between iris 14 and natural lens 16. IOLs of the present invention are preferably implanted in anterior chamber 6 to correct refractive errors while healthy natural lens 16 remains in place (phakic application). IOLs of the present invention may also be implanted in posterior chamber 8, and may be used in aphakic eyes as a replacement for a diseased natural lens 16 such as for example following cataract surgery. Eye 10 also includes an optical axis OA—OA that is an imaginary line that passes through the optical centers 20 of anterior surface 22 and posterior surface 24 of lens 16. Optical axis OA—OA in the human eye 10 is generally perpendicular to a portion of cornea 12, natural lens 16 and retina 18.

Figure 2:
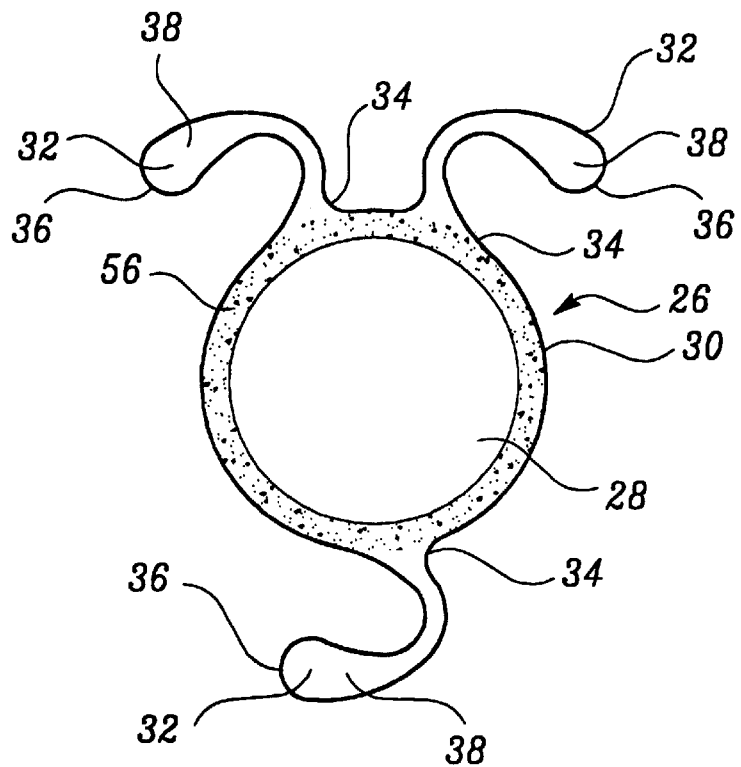
FIG. 2 is a plan view of an IOL made in accordance with the present invention.
Figure 3:
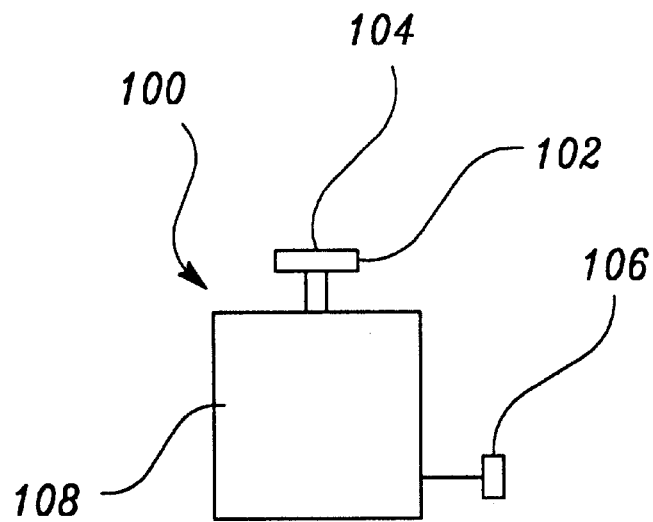
FIG. 3 is a side view of machining equipment.
Figure 4:
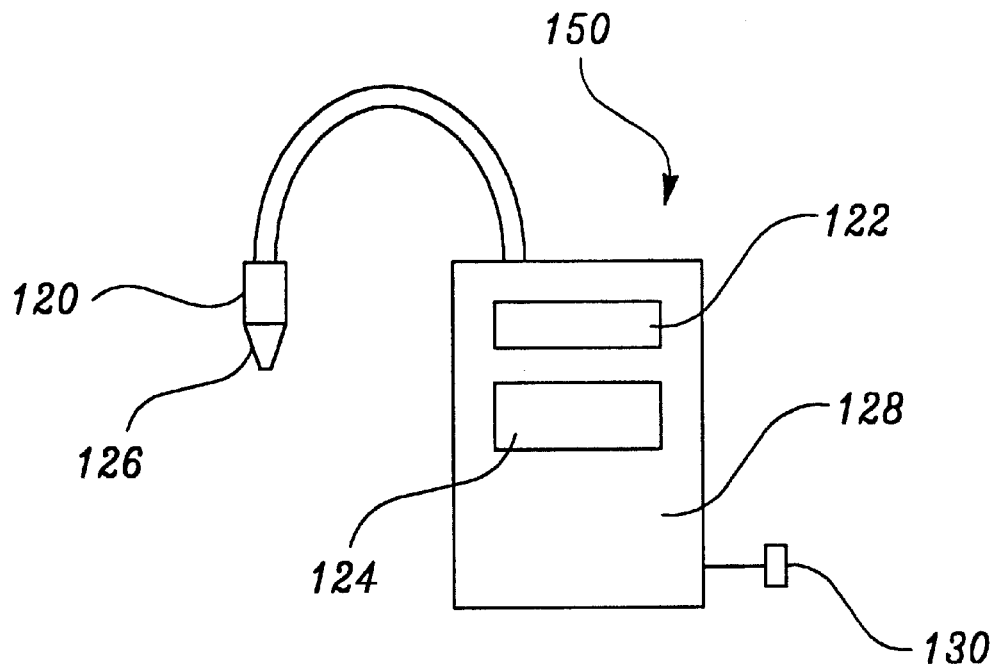
FIG. 4 is a side View of abrasion equipment.

An IOL, identified by reference numeral 26, produced using the process of the present invention is illustrated in FIG. 2. IOL 26 is designed for implantation preferably in anterior chamber 6 of a patient's eye 10. IOL 26 has an optic portion 28 with an outer peripheral edge 30. Three separate haptic elements 32, each having an inner portion 34 and an outer tip 36, are connected by inner portions 34 to outer peripheral edge 30 of optic portion 28. Each haptic element 32 also includes a broadened contact plate 38 designed to engage inner surfaces 40 in anterior chamber 6 or inner surfaces 42 in posterior chamber 8 of eye 10. Haptic elements 32 may be integrally formed with optic portion 28 or alternatively, haptic elements 32 may be attached to optic portion 28 by staking, chemical polymerization or other methods known to those skilled in the art. A glare reduction zone 56 is adjacent to outer peripheral edge 30 for reducing glare when outer peripheral edge 30 of IOL 26 is struck by light enter eye 10 during high light or at other times when pupil 58 is dilated.

In accordance with the present invention, haptic elements 32 are designed so that when IOL 26 is implanted in a patient's eye 10, IOL 26 is held in place through compressive forces exerted by inner surfaces 40 or 42 on outer tips 36 of haptic elements 32.

Glare reduction zone 56 is produced on the outer peripheral edge 30 of IOL 26 through the process of the present invention whereby a highly regulated low-pressure spray of powder is applied to the surface of IOL 26 in the desired location. The present process includes machining or lathing IOL 26 in accordance with methods commonly known to those skilled in the art. Prior to polishing and cleaning IOL 26, the same is removably attached to upper surface 104 of motor 108 driven rotating head 102 of machining equipment 100. Machining equipment 100 is attached to a power source through plug 106. IOL 26 may be removably attached to rotating head 102 using wax, clamps, vacuum or any like method. Once attached to rotating head 102, portions of the exposed surface of optic portion 28 may be removably covered with a suitable protective mask or plug such as a soft yet machinable thermoplastic material. Suitable machinable thermoplastic materials include but are not limited to Delrin™, E.I. duPont de Nemours & Company, Inc., or Teflon™, E.I. duPont de Nemours & Company, Inc. In choosing a material to mask IOL 26, a material softer than that of IOL 26 is preferred so that the mask does not create defects on the surface of IOL 26. Any portion of IOL 26 to be protected from the effects of powder may be protected with a protective mask. However, due to the highly regulated spray of powder delivered by the preferred equipment described in detail below, a protective mask is unnecessary in most instances.

Rotating head 102 is rotated at approximately 5 to 50 revolutions per minute, but preferably approximately 5 to 30 revolutions per minute and most preferably 10 to 15 revolutions per minute for more even etching of optic portion 28 to produce glare reduction zone 56. Once rotating head 102 begins rotating at the desired speed, a powder is sprayed adjacent outer peripheral edge 30 on anterior surface 44 of IOL 26. Optionally, both anterior surface 22 and posterior surface 46 may be etched using the present process although not necessary in most instances to achieve a non-glare surface. The preferred powder is 30-micron aluminum oxide because it is superior to other powders in staying suspended in air. However, other suitable powders are available such as 60-micron silica and powders similar thereto. The powder is sprayed with motor 128 driven abrasion equipment 150 adjacent outer peripheral edge 30. Abrasion equipment 150 is connected to a power source through plug 130. The powder is sprayed using a stationary handpiece device 120 having an air/powder mixturing system 122 and regulator 124 to allow computer programmable parameters to adjust the velocity and density of the powder to be applied to the anterior surface 44 and/or posterior surface 46 of IOL 26. Preferably the abrasive media or powder is applied at approximately 20 to 60 pounds per square inch of pressure, but preferably approximately 30 to 50 pound per square inch of pressure and most preferably approximately 40 pounds per square inch of pressure. In applying the powder to IOL 26 nozzle 126 of handpiece device 120 is preferably maintained at approximately 2 to 6 mm, but preferably at approximately 2 to 4 mm and most preferably 3 mm from the surface of IOL 26 for approximately 5 to 60 seconds but preferably 10 to 50 seconds and most preferably 15 to 20 seconds to impart an evenly etched or "frosted" glare reduction zone 56. Important to note, the powder, force, revolutions per minute, nozzle distance, and duration of process will vary depending on the degree of etching desired, IOL material used and the particular IOL style being processed.

Optionally, rather than attaching IOL 26 to rotating head 102 and applying glare reduction zone 56 with stationary nozzle 126, IOL 26 may be held stationary as nozzle 126 is rotated adjacent outer peripheral edge 30.

The preferred abrasion equipment 150 is The Director +™ model MicroPrep® air abrasion cavity preparation system manufactured by Lares Research, Chico, Calif. 95973. Other suitable model air abrasion cavity preparation systems include but are not limited to The Associate +™ and The Producer™ each also manufactured by Lares Research, Chico, Calif. 95973.

The nozzle 126 of the preferred abrasion equipment 150 must be altered for purposes of the subject application. Abrasion equipment 150 is typically manufactured having a tungsten nozzle 126 made of carbide. Such a nozzle 126 is unsuitable for the subject application due to rapid degradation thereof in the manufacturing setting. Continual periodic replacement of rapidly degrading nozzle 126 is both costly and has the potential of contaminating IOL 26 with tungsten particles. Accordingly, nozzle 126 is customized for purposes of the present invention and manufactured from ceramic.

Once glare reduction zone 56 of approximately 0.2 to 1.0 mm, but preferably approximately 0.2 to 0.6 mm and most preferably approximately 0.2 to 0.4 mm is etched adjacent to outer peripheral edge 30 on preferably the anterior surface 44 of IOL 26, IOL 26 is polished, cleaned, sterilized and packaged as commonly known to those skilled in the art.

The subject air abrasive texturing process is suitable for use if desired on ophthalmic devices or implants such as for example but not limited to IOLs, corneal inlays, corneal rings, capsular bag extension rings and the like formed from acrylates, methacrylates, hydrogels, and like machinable materials. In most cases, the subject process is not suitable for use on most molded materials such as silicones used in the production of ophthalmic devices such as IOLs.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

I claim:

1. A method of etching a portion of an intraocular implant comprising:
    rotating an intraocular implant, and
    spraying the intraocular implant with an abrasive material to impart an evenly etched glare resistant zone.

2. A method of etching a portion of an intraocular implant comprising:
    rotating an abrasive material spray about a surface of an intraocular implant to impart an evenly etched glare resistant zone.

3. The method of claim 1 wherein said intraocular implant is rotated at a speed of approximately 5 to 50 revolutions per minute.

4. The method of claim 1 wherein said intraocular implant is rotated at a speed of approximately 10 to 15 revolutions per minute.

5. The method of claim 1 or 2 wherein said abrasive material is a powder.

6. The method of claim 1 or 2 wherein said abrasive material is selected from the group consisting of aluminum oxide and silica.

7. The method of claim 1 or 2 wherein said abrasive material is 30 micron aluminum oxide.

8. The method of claim 1 or 2 wherein said abrasive material is sprayed at a force of approximately 20 to 60 pounds per square inch.

9. The method of claim 1 or 2 wherein said abrasive material is sprayed at a force of approximately 40 pounds per square inch.

10. The method of claim 1 or 2 wherein said abrasive material is sprayed on the intraocular implant for approximately 5 to 60 seconds.

11. The method of claim 1 or 2 wherein said abrasive material is sprayed on the intraocular implant for approximately 15 to 20 seconds.

12. The method of claim 1 or 2 wherein said abrasive material is sprayed from a ceramic nozzle at a distance of approximately 2 to 6 mm from said intraocular implant.

13. The method of claim 1 or 2 wherein said abrasive material is sprayed from a ceramic nozzle at a distance of approximately 3 mm from said intraocular implant.

14. The method of claim 1 or 2 wherein a portion of said intraocular implant is masked with a thermoplastic material.

15. The method of claim 1 or 2 wherein a portion of said intraocular implant is etched adjacent to an outer peripheral edge to impart said glare resistant zone.

16. The method of claim 1 or 2 wherein an approximately 0.2 to 1.0 mm portion of said intraocular implant is etched adjacent to an outer peripheral edge to impart said glare resistant zone.

17. The method of claim 1 or 2 wherein an approximately 0.2 to 0.4 mm portion of said intraocular implant is etched adjacent to an outer peripheral edge to impart said glare resistant zone.

18. The method of claim 2 wherein said spray is rotated at a speed of approximately 5 to 50 revolutions per minute.

19. The method of claim 2 wherein said spray is rotated at a speed of approximately 10 to 15 revolutions per minute.

20. The method of claim 1 or 2 wherein said abrasive material is 60 micron silica.

21. An intraocular implant produced using a process for etching a portion thereof comprising:
    rotating said intraocular implant, and
    spraying said intraocular implant with an abrasive material to impart an evenly etched glare resistant zone.

22. An intraocular implant produced using a process for etching a portion thereof comprising:
    rotating an abrasive material spray about a surface of said intraocular implant to impart an evenly etched glare resistant zone.

23. The intraocular implant of claim 21 wherein said intraocular implant is rotated at a speed of approximately 5 to 50 revolutions per minute.

24. The intraocular implant of claim 21 wherein said intraocular implant is rotated at a speed of approximately 10 to 15 revolutions per minute.

25. The intraocular implant of claim 21 or 22 wherein said abrasive material is a powder.

26. The intraocular implant of claim 21 or 22 wherein said abrasive material is selected from the group consisting of aluminum oxide and silica.

27. The intraocular implant of claim 21 or 22 wherein said abrasive material is 30 micron aluminum oxide.

28. The intraocular implant of claim 21 or 22 wherein said abrasive material is sprayed at a force of approximately 20 to 60 pounds per square inch.

29. The intraocular implant of claim 21 or 22 wherein said abrasive material is sprayed at a force of approximately 40 pounds per square inch.

30. The intraocular implant of claim 21 or 22 wherein said abrasive material is sprayed on the intraocular implant for approximately 5 to 60 seconds.

31. The intraocular implant of claim 21 or 22 wherein said abrasive material is sprayed on the intraocular implant for approximately 15 to 20 seconds.

32. The intraocular implant of claim 21 or 22 wherein said abrasive material is sprayed from a ceramic nozzle at a distance of approximately 2 to 6 mm from said intraocular implant.

33. The intraocular implant of claim 21 or 22 wherein said abrasive material is sprayed from a ceramic nozzle at a distance of approximately 3 mm from said intraocular implant.

34. The intraocular implant of claim 21 or 22 wherein a portion of said intraocular implant is masked with a thermoplastic material.

35. The intraocular implant of claim 21 or 22 wherein a portion of said intraocular implant is etched adjacent to an outer peripheral edge to impart said glare resistant zone.

36. The intraocular implant of claim 21 or 22 wherein an approximately 0.2 to 1.0 mm portion of said intraocular implant is etched adjacent to an outer peripheral edge to impart said glare resistant zone.

37. The intraocular implant of claim 21 or 22 wherein an approximately 0.2 to 0.4 mm portion of said intraocular implant is etched adjacent to an outer peripheral edge to impart a glare resistant zone.

38. The intraocular implant of claim 22 wherein said spray is rotated at a speed of approximately 5 to 50 revolutions per minute.

39. The intraocular implant of claim 22 wherein said spray is rotated at a speed of approximately 10 to 15 revolutions per minute.

40. The intraocular implant of claim 21 or 22 wherein said abrasive material is 60 micron silica.

41. A method of etching a portion of an intraocular lens comprising:
   rotating an intraocular lens, and
   spraying the intraocular lens with an abrasive material to impart an evenly etched glare resistant zone.

42. A method of etching a portion of an intraocular lens comprising:
   rotating an abrasive material spray about a surface of an intraocular lens to impart an evenly etched glare resistant zone.

43. The method of claim 41 wherein said intraocular lens is rotated at a speed of approximately 5 to 50 revolutions per minute.

44. The method of claim 41 wherein said intraocular lens is rotated at a speed of approximately 10 to 15 revolutions per minute.

45. The method of claim 41 or 42 wherein said abrasive material is a powder.

46. The method of claim 41 or 42 wherein said abrasive material is selected from the group consisting of aluminum oxide and silica.

47. The method of claim 41 or 42 wherein said abrasive material is 30 micron aluminum oxide.

48. The method of claim 41 or 42 wherein said abrasive material is sprayed at a force of approximately 20 to 60 pounds per square inch.

49. The method of claim 41 or 42 wherein said abrasive material is sprayed at a force of approximately 40 pounds per square inch.

50. The method of claim 41 or 42 wherein said abrasive material is sprayed on the intraocular lens for approximately 5 to 60 seconds.

51. The method of claim 41 or 42 wherein said abrasive material is sprayed on the intraocular lens for approximately 15 to 20 seconds.

52. The method of claim 41 or 42 wherein said abrasive material is sprayed from a ceramic nozzle at a distance of approximately 2 to 6 mm from said intraocular lens.

53. The method of claim 41 or 42 wherein said abrasive material is sprayed from a ceramic nozzle at a distance of approximately 3 mm from said intraocular lens.

54. The method of claim 41 or 42 wherein a portion of said intraocular lens is masked with a thermoplastic material.

55. The method of claim 41 or 42 wherein a portion of said intraocular lens is etched adjacent to an outer peripheral edge to impart said glare resistant zone.

56. The method of claim 41 or 42 wherein an approximately 0.2 to 1.0 mm portion of said intraocular lens is etched adjacent to an outer peripheral edge to impart said glare resistant zone.

57. The method of claim 41 or 42 wherein an approximately 0.2 to 0.4 mm portion of said intraocular lens is etched adjacent to an outer peripheral edge to impart a glare resistant zone.

58. The method of claim 42 wherein said spray is rotated at a speed of approximately 5 to 50 revolutions per minute.

59. The method of claim 42 wherein said spray is rotated at a speed of approximately 10 to 15 revolutions per minute.

60. The method of claim 41 or 42 wherein said abrasive material is 60 micron silica.

61. An intraocular lens produced using a process for etching a portion thereof comprising:
   rotating said intraocular lens, and
   spraying said intraocular lens with an abrasive material to impart an evenly etched glare resistant zone.

62. An intraocular lens produced using a process for etching a portion thereof comprising:
   rotating an abrasive material spray about a surface of said intraocular lens to impart an evenly etched glare resistant zone.

63. The intraocular lens of claim 61 wherein said intraocular lens is rotated at a speed of approximately 5 to 50 revolutions per minute.

64. The intraocular lens of claim 61 wherein said intraocular lens is rotated at a speed of approximately 10 to 15 revolutions per minute.

65. The intraocular lens of claim 61 or 62 wherein said abrasive material is a powder.

66. The intraocular lens of claim 61 or 62 wherein said abrasive material is selected from the group consisting of aluminum oxide and silica.

67. The intraocular lens of claim 61 or 62 wherein said abrasive material is 30 micron aluminum oxide.

68. The intraocular lens of claim 61 or 62 wherein said abrasive material is sprayed at a force of approximately 20 to 60 pounds per square inch.

69. The intraocular lens of claim 61 or 62 wherein said abrasive material is sprayed at a force of approximately 40 pounds per square inch.

70. The intraocular lens of claim 61 or 62 wherein said abrasive material is sprayed on the intraocular lens for approximately 5 to 60 seconds.

71. The intraocular lens of claim 61 or 62 wherein said abrasive material is sprayed on the intraocular lens for approximately 15 to 20 seconds.

72. The intraocular lens of claim 61 or 62 wherein said abrasive material is sprayed from a ceramic nozzle at a distance of approximately 2 to 6 mm from said intraocular lens.

73. The intraocular lens of claim 61 or 62 wherein said abrasive material is sprayed from a ceramic nozzle at a distance of approximately 3 mm from said intraocular lens.

74. The intraocular lens of claim 61 or 62 wherein a portion of said intraocular lens is masked with a thermoplastic material.

75. The intraocular lens of claim 61 or 62 wherein a portion of said intraocular lens is etched adjacent to an outer peripheral edge to impart said glare resistant zone.

76. The intraocular lens of claim 61 or 62 wherein an approximately 0.2 to 1.0 mm portion of said intraocular lens is etched adjacent to an outer peripheral edge to impart said glare resistant zone.

77. The intraocular lens of claim 61 or 62 wherein an approximately 0.2 to 0.4 mm portion of said intraocular lens is etched adjacent to an outer peripheral edge to impart said glare resistant zone.

78. The intraocular lens of claim 62 wherein said spray is rotated at a speed of approximately 5 to 50 revolutions per minute.

79. The intraocular lens of claim 62 wherein said spray is rotated at a speed of approximately 10 to 15 revolutions per minute.

80. The intraocular lens of claim 61 or 62 wherein said abrasive material is 60 micron silica.

\* \* \* \* \*